United States Patent
Schilp et al.

(10) Patent No.: US 8,734,315 B2
(45) Date of Patent: May 27, 2014

(54) APPARATUS AND METHOD FOR FILLING A MEDICAL INSTRUMENT WITH A RADIOACTIVE SUBSTANCE

(75) Inventors: Michael Schilp, Garching (DE); Nikula Tuomo, Ottobrunn (DE); Oliver Buck, Bayerisch Gmain (DE)

(73) Assignee: Isotopen Technologien Munchen AG, Garching (DE)

( * ) Notice: Subject to any disclaimer, the term of this patent is extended or adjusted under 35 U.S.C. 154(b) by 994 days.

(21) Appl. No.: 12/526,429

(22) PCT Filed: Feb. 1, 2008

(86) PCT No.: PCT/EP2008/000825
§ 371 (c)(1),
(2), (4) Date: Aug. 28, 2009

(87) PCT Pub. No.: WO2008/095655
PCT Pub. Date: Aug. 14, 2008

(65) Prior Publication Data
US 2010/0006156 A1 Jan. 14, 2010

(30) Foreign Application Priority Data
Feb. 7, 2007 (DE) .......... 10 2007 006 189

(51) Int. Cl.
*A61M 36/06* (2006.01)
*A61M 36/08* (2006.01)

(52) U.S. Cl.
USPC ............................... 600/4; 600/5

(58) Field of Classification Search
CPC .......... A61N 2005/1021; B65B 3/003; B65B 3/006; A61M 5/1785
USPC ............................ 600/1–8; 250/428–432 PD, 250/496.1–498.1, 506.1–507.1
See application file for complete search history.

(56) References Cited

U.S. PATENT DOCUMENTS

| | | | |
|---|---|---|---|
| 4,208,588 A * | 6/1980 | Rudin ...................... 250/496.1 |
| 4,241,728 A | 12/1980 | Mirell | |
| 4,401,108 A | 8/1983 | Galkin et al. | |
| 5,309,959 A | 5/1994 | Shaw et al. | |
| 5,961,439 A | 10/1999 | Chernomorsky et al. | |
| 6,162,198 A | 12/2000 | Coffey et al. | |
| 6,450,936 B1 | 9/2002 | Smith, III et al. | |
| 6,494,824 B1 * | 12/2002 | Apple et al. ................... 600/3 |
| 2003/0216609 A1 | 11/2003 | Dell et al. | |
| 2004/0015038 A1 * | 1/2004 | Lemer ........................... 600/5 |
| 2005/0085682 A1 * | 4/2005 | Sasaki et al. .................. 600/4 |
| 2005/0203329 A1 * | 9/2005 | Muto et al. .................... 600/1 |
| 2008/0142743 A1 * | 6/2008 | Tartaglia ................... 250/515.1 |
| 2010/0030009 A1 * | 2/2010 | Lemer ........................... 600/4 |

FOREIGN PATENT DOCUMENTS

| | | | |
|---|---|---|---|
| JP | H-0650653 | 7/1994 | |
| JP | 2002-210007 | 7/2002 | |
| RU | 2110214 | 5/1998 | |
| WO | WO 94/04415 | 3/1994 | |
| WO | WO-99-42165 | 8/1999 | |
| WO | WO-2006-108026 | 10/2006 | |
| WO | WO 2006108026 A2 * | 10/2006 | ............. G06F 19/00 |

* cited by examiner

*Primary Examiner* — Catherine B Kuhlman
(74) *Attorney, Agent, or Firm* — Saliwanchik, Lloyd & Eisenschenk (57) ABSTRACT

An apparatus for filling a medical instrument with a radioactive substance, said apparatus including a housing designed to receive a syringe and at least part of a medical instrument and to shield against radioactive radiation, further including a means to take up a receptacle for a radioactive substance.

30 Claims, 4 Drawing Sheets

APPARATUS AND METHOD FOR FILLING A MEDICAL INSTRUMENT WITH A RADIOACTIVE SUBSTANCE

CROSS-REFERENCE TO RELATED APPLICATION

This application is the U.S. National Stage Application of International Patent Application No. PCT/EP2008/000825, filed Feb. 1, 2008, which claims the benefit of German Application Serial No. 102007006189.9, filed Feb. 7, 2007, both of which are hereby incorporated by reference herein in their entirety, including any figures, tables, or drawings.

The instant invention relates to an apparatus for filling a medical instrument with a radioactive substance and a corresponding method.

In nuclear medicine, radioactive substances are used for various diagnostic and therapeutic purposes. To name an example, in angioplasty a stricture or blockage of blood vessels in a human or animal body is removed or the vessel reopened by way of balloon dilation. There is a great risk that scars may form (recurrent stenosis) after introduction of a balloon catheter into a blood vessel and dilating or reopening the blood vessel, caused by microscopic lesion of the inner wall of the blood vessel during the procedure. To preclude cicatrization, a stent imbued with a medicinal substance may be placed at the widened location in the blood vessel. The cell growth inhibitors continuously released by the same will prevent restenosis. A promising alternative consists in filling a dilation balloon with a radioactive liquid. The radioactive radiation which emanates from the same will cause local obliteration of the walls of the affected vessel so that cicatrization thus can be avoided. By applying radioactive radiation, the risk of restenosis can be lowered many times in comparison with dilation or reopening of a blood vessel and thereafter leaving it untreated. What is more, this is achieved without submitting the patient's body to a poison load from medication. However, specific requirements must be met and preventive measures be taken in the clinical environment when making use of radioactive radiation. For instance, filling the catheter with radioactive liquids presents an increased hazard both for the patient and the medical staff.

Normally, catheters applied in radioactive treatment are filled manually, using a syringe. Treatment, as a rule, comprises filling the syringe with a fluid radioactive substance from a receptacle, usually performed in a laboratory, transporting the syringe filled with the radioactive liquid to the patient, applying a catheter, this being done by a physician, and connecting the catheter to the syringe to fill it, emptying the catheter, and removing the catheter from inside the patient. Once the syringe has been filled, the physician and clinical staff as well as the patient are exposed to the radioactive radiation issuing from the radioactive liquid. The patient, moreover, suffers from radiation exposure before and after the actual treatment of the blood vessel during the filling and emptying of the catheter, a risk of further radiation exposure already existing while the syringe filled with the radioactive liquid is transported from the laboratory to the patient.

It is an object of the instant invention to provide an apparatus for and a method of filling a medical instrument, such as a catheter, by means of which apparatus and method the radiation exposure of patients and clinical staff can be reduced, particularly while the medical instrument is being filled.

These objects are met by an apparatus comprising the features recited in claim 1 and a method comprising the features recited in claim 17.

Advantageous embodiments are indicated in the dependent claims.

In accordance with the invention, an apparatus is provided for filling a medical instrument with a radioactive substance. The apparatus includes a housings which shields radioactive radiation and is designed to receive a syringe and at least part of a medical instrument. It further includes a means to take up a receptacle for a radioactive substance.

With the apparatus according to the invention a substantial reduction can be obtained in radiation exposure caused by a radioactive substance, especially a radioactive liquid which is being filled into a medical instrument, for example, a catheter, in particular a balloon catheter. This is so because the apparatus is designed such that the filling and emptying of the medical instrument is performed in a radiation-shielding housing. With the apparatus according to the invention, a syringe used to fill the medical instrument and at least part of the medical instrument as well as a receptacle containing a radioactive substance for administration can be interconnected in a way which safeguards against radiation. Therefore, the medical staff applying or preparing the treatment as well as the patient are substantially protected from radioactive radiation while the catheter is being filled or emptied. The syringe, the catheter, and the receptacle containing the radioactive substance can be interconnected and shielded before the catheter is filled. In this manner, transportation without shielding of a syringe filled with a radioactive substance can be avoided.

According to a preferred embodiment, the means destined to take up the receptacle is devised for positioning and fixing of the receptacle outside of the housing. And the housing has an opening for a connection to be established with the receptacle for feeding a radioactive substance into the housing. In this way, receptacles in which radioactive substances are kept can be connected to the housing regardless of their size and, moreover, the apparatus can be designed in space-saving fashion since the receptacle need not be received inside the housing of the apparatus. For transportation and storage of a radioactive substance, the receptacle itself preferably is equipped with its own radioactive shielding or made of a material which offers such shielding. For this reason, positioning of the receptacle inside the shielded housing as such offers no advantages. Yet such an embodiment of the apparatus is conceivable as well. The fact that the apparatus and the receptacle may be embodied by separate units makes easy and riskfree handling and filling of the radioactive substance possible. It may be accomplished, for example, in a laboratory by skilled personnel using suitable equipment. Physicians or other medical staff need not be bothered with this task.

According to another preferred embodiment, the housing comprises a lid which serves for covering or closing of the apparatus and of a receptacle for a radioactive substance arranged at the housing. With the open lid, it is possible to put components, such as a syringe, a medical instrument, valves, and tube sections for connections into the housing and to interconnect the components. The radioactive substance, on the other hand, preferably is not fed into the syringe and medical instrument, respectively, until after the lid has been closed.

As explained, the lid design is such that also the receptacle for the radioactive substance can be covered or closed by the lid. Therefore, the design of the receptacle may be such that a cover of the receptacle, once the receptacle is positioned on the apparatus, may be removed and one or more tubes be used to interconnect the receptacle, syringe, and medical instrument, whereupon all the components, including the receptacle will be shielded against radioactive radiation upon closing the lid.

It is likewise conceivable to provide a lid which closes only the housing of the apparatus but not the receptacle. With this embodiment, the receptacle could be provided with a conduit protected against radioactive radiation for connection to the housing.

According to another preferred embodiment, the housing comprises a means adapted to be operated from outside, for example, a rotary lever which extends through the wall of the housing and may be engaged for manipulating a valve mounted inside the housing. The valve, for example, may be made of plastics such as frequently used in the medical field to connect hoses. In particular, it may be a three-way or multi-way valve and be arranged in the housing for actuation from outside by the rotary lever.

According to another preferred embodiment, the housing is made of a material which shields radioactive radiation, especially of tungsten. Other materials suitable for radiation shielding may be chosen as well.

According to yet another embodiment, the housing may comprise a window opening. A lead window pane may be mounted in the window opening. Thus it is possible, with the lid closed, to watch the procedure of filling a syringe to make sure, for instance, that the liquid drawn up is free of bubbles. Alternatively or additionally, the housing may comprise a flap by which to close the window. The flap, in addition, may be provided with a mirror at the inside so that the filling procedure may be watched when the flap is partly opened. The radioactive liquid must not contain bubbles. That is extremely important since the presence of air in the catheter tube might prohibit the complete filling of the catheter so that the balloon would become partly or totally filled with air and the radioactive liquid remain in the tube. In this event, no treatment of the blood vessel at the desired location would happen.

In accordance with a further embodiment, the housing is designed for fixing of the syringe and part of the medical instrument and also for receiving and fixing one or more valves and connecting lines in the housing. Arranging and fixing the components may be accomplished, for example, by the provision of form-fit holding devices in the interior of the housing to retain the respective components or parts in place. Such holding devices may be manufactured as inserts to be introduced into the housing or they may be made internal with the housing. It is conceivable, too, that parts of the holding devices are provided both in the lid and the remainder of the housing so that full fixation of the component(s) positioned in the housing is obtained by closing of the lid.

In accordance with yet another embodiment, the housing includes an opening for actuating an injection plunger of a syringe disposed in the apparatus. The syringe disposed in the apparatus thus may be operated manually or by means of a motor from the outside of the housing.

Moreover, a shielding device may be provided for the end of the injection plunger projecting from the syringe. A shielding device, for example, may be adapted for connection to the end of the injection plunger and be movably arranged in an opening of the housing or for being slipped onto the injection plunger or otherwise connected to the same. Furthermore, the shielding device for the injection plunger may be embodied by an extension of the injection plunger. Preferably, the shielding device for the injection plunger is made of the same material as the housing of the apparatus and the apparatus itself, respectively. It might also be made simply as an extension of the injection plunger without any specific shielding properties. Moreover, the housing of the apparatus may include an opening for passage of a medical instrument or parts thereof.

Finally, the apparatus according to another preferred embodiment may include a support connected to the apparatus in such a way that the apparatus and a syringe disposed in the apparatus are inclined with respect to a base surface, e.g. a table top. The inclination of the apparatus, preferably, is chosen so that a syringe disposed in the apparatus is inclined in downward direction. Hereby, air bubbles may rise towards the end of the syringe and thus not get into the catheter.

According to another preferred embodiment, the medical instrument is a balloon catheter.

The invention also provides a system for filling a receptacle with a radioactive substance, including an apparatus according to the invention, a receptacle for a radioactive substance, and a syringe.

In accordance with an embodiment, the system further may include a salve disposed in the apparatus, a medical instrument, such as a catheter, disposed at least partly in the apparatus, and tube sections for connecting the syringe, the valve, the receptacle for a radioactive substance, and the medical instrument. In such a system, a syringe, a receptacle for a radioactive substance, and a medical instrument may be interconnected by tube sections and valves in such manner that switching a valve, in particular a three-way valve, first will cause filling of the syringe with the radioactive liquid and then filling of a medical instrument big the emptying of the syringe. During this procedure, the syringe, the receptacle for the radioactive substance, and the tube section or sections and the valve or valves as well as at least part of the medical instrument are shielded with respect to the surroundings. Hereby, exposure to radioactive radiation of persons in the vicinity can be greatly reduced.

According to another preferred embodiment, the receptacle for a radioactive substance is removably attached to the apparatus. The receptacle thus is readily exchangeable and yet forms a stable unit with the apparatus. The apparatus together with the receptacle, therefore, can be shifted or transferred easily with one hand. Moreover, the apparatus can be connected to receptacles of different sizes.

The invention, furthermore, provides a filling method for a radioactive substance. The method includes introducing a syringe into an apparatus according to the invention, arranging a receptacle containing a radioactive substance at the apparatus, and drawing a radioactive substance into the syringe. According to a preferred embodiment, the method may include arranging a medical instrument, such as catheter, or part thereof in the apparatus and filling the catheter with a radioactive substance from the syringe. Persons who carry out the filling of the medical instrument as well as patients who are to receive treatment are better protected against radioactive radiation by the arrangement of the syringe and part of the medical instrument or the entire one as well as the tube sections for connecting the syringe and the medical instrument to a receptacle for a radioactive substance, and the valves disposed in between. In this manner, the radiation dose absorbed per treatment by the persons receiving the treatment can be reduced. On the one hand, this diminishes the health hazard of the persons in question. On the other hand, the admissible number of treatments performed may be increased in view of the lesser radiation exposure. Filling of the syringe may be accomplished while making use of a shielding means for the end of the injection plunger which protrudes from the syringe. Hereby the radiation exposure can be reduced still further.

The invention will be described further, by way of example, with reference to the accompanying drawings, in which.

The apparatus according to the invention will described below with reference to the embodiment illustrated in the drawings. As may be taken particularly from FIG. 1, the apparatus includes a housing 1 and a lid 2 connected to the same by hinges 3. The lid 2 can be tilted onto the housing to close it. The lid 2 moreover is equipped with rotary, levers 4, 5 which pass through the lid and each are provided at the inside with an engaging fixture 6 and 7, respectively, for valve levers. Rotary levers may be provided, in addition or alternatively, in the wall of the housing.

The lid 2 further comprises a portion 2a which projects beyond the side of the housing 1 when the lid is folded down on the housing. This portion serves to cover or close, respectively, a receptacle 8 in which radioactive liquid may be received. A window opening 9 is formed in the lid 2. A window pane (not shown) may be disposed in the window opening 9. It may be made, for example, of lead glass for purposes of shielding radioactive radiation. As may be seen in FIG. 1, a syringe 10 is positioned in the interior of a housing 1 from which it is removable. The syringe may be any conventional syringe, such as a disposable plastic syringe or a multiple use glass syringe. Inside the housing 1, furthermore, there is a web-shaped receiving fixture 11 extending transversely of the longitudinal direction of the housing and serving to receive the tip of the syringe 10 in form-lock engagement in a corresponding U-shaped depression. The receiving fixture 11 is mounted at such spacing from a front end wall of the housing 1 that the syringe 10 can be introduced between the receiving fixture 11 and the front end wall of the housing 1, with an injection plunger 13 of the syringe 10 protruding to the outside through an opening 14 formed in the wall of the housing 1. As may be gathered from FIG. 1, the distance between the receiving fixture 11 and the front end opening in the housing is chosen to correspond to the length of the syringe body. Accordingly, the end of the syringe body abuts against the front end wall of the housing when the syringe 10 is inserted in the housing.

Figure 1:
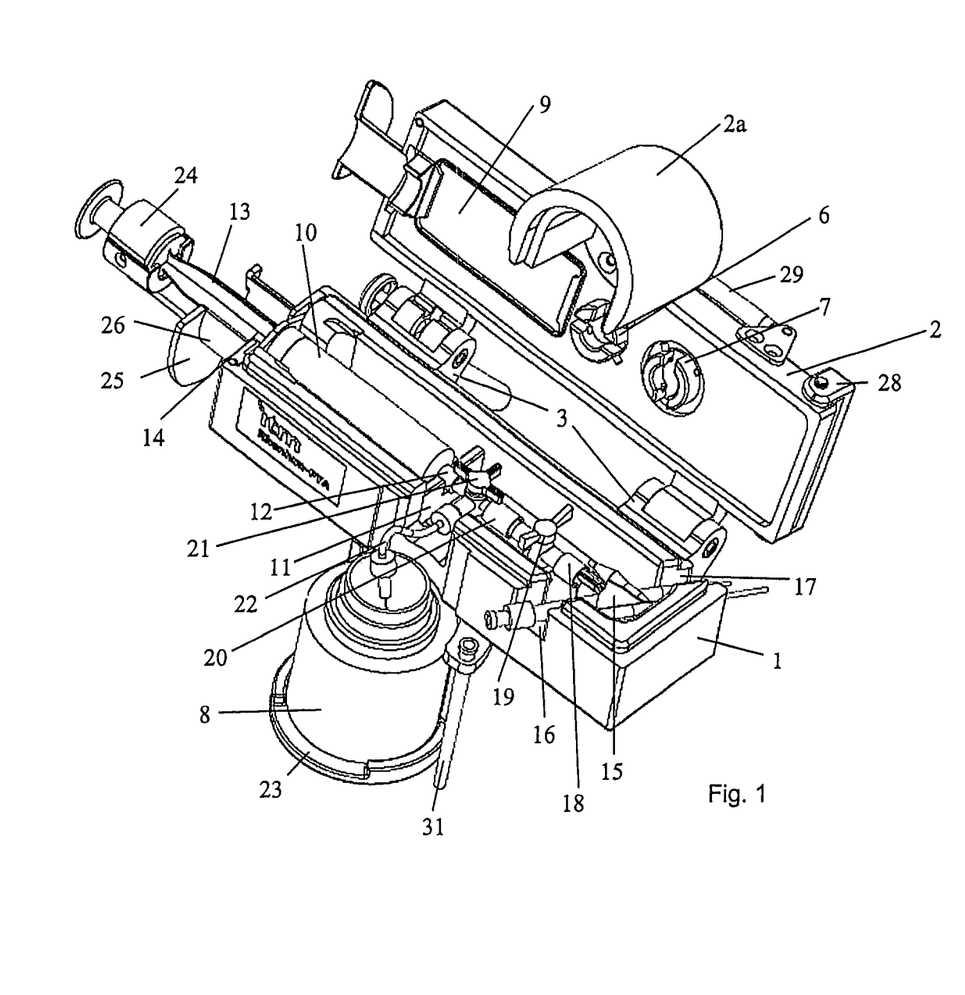
FIG. 1 is a perspective view from above of an apparatus according to the invention, in open position.

FIG. 1 also depicts part of a medical instrument 15, for example, a balloon catheter disposed in the housing close to the wall of the housing opposite the front end wall which is formed with the opening 14 for the injection plunger 13. The wall of the housing is formed with two more openings 16, 17 for passage of the medical instrument 15 to allow that part of the medical instrument 15 which comprises a T-shaped branching to be placed in the housing. The end of the branching of the medical instrument 15 disposed in the interior of the housing 1 is connected by a tube section 18 to a valve 19 which comes to be engaged with the fixture 7 formed accordingly of the rotary lever 5, upon closing of the lid 2. The valve 19 also is connected, by another tube section 20, to a three-way valve 21 which enters into engagement with the fixture 6 of the rotary lever 4 when the lid 2 is closed. The three-way valve 21 is connected through another tube section 22 with the receptacle 8 for a radioactive substance, the receptacle being disposed in a take-up device 23 at the housing 1. The receptacle 8 may be removed from the take-up 23 at the housing. Connection between the medical instrument 15, the valves 19, 21, the tube sections 18, 20, 22, and the syringe 10 preferably is established by Luer Lock connections or plug connections.

FIG. 1 further shows a shielding device 24 for the end of the injection plunger 13 protruding from the syringe 10. The shielding device 24 is connected to the end of the injection plunger 13 and its design is such that it may be slipped from the side onto the disc-shaped end of the injection plunger 13. The shielding device 24 preferably consists of the same material as the housing 1 of the apparatus, being made for instance of tungsten. However, it may also be made of a different material. As may be seen in FIG. 1, the shielding device 24 is an extension of the injection plunger 13. The idea is that this manner the finger of the person actuating the injection plunger 13 can be located at a greater distance from the radioactive liquid received in the syringe 10. In addition, also the material of the shielding device 24 serves for radiation shielding.

Figure 2:
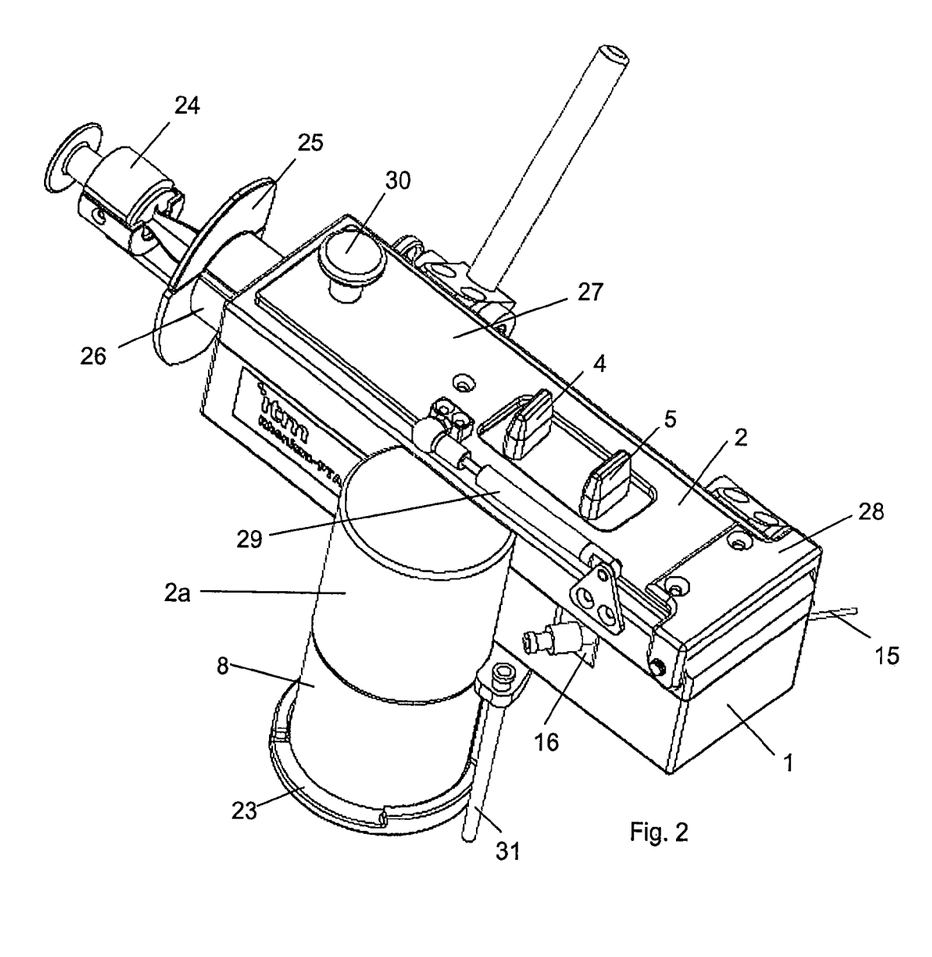
FIG. 2 is a perspective view from above of the apparatus according to the invention shown in FIG. 1, in closed position.

The apparatus, moreover, includes an annular holding surface 25 located at the end of a tubular portion 26 which is an extension of the housing and surrounds the injection plunger 13. It is the purpose of the holding surface 25 positioned vertically with respect to the tubular portion 26 to allow the syringe 10 inserted in the housing 1 to be operated with the fingers of just one hand. As illustrated in FIGS. 1 and 2, the holding surface 25 and the tubular portion 26 surrounding the injection plunger 13 are composed of two pieces disposed at the housing and at the lid 2 and complementing each other to present one part after the lid 2 has been closed.

FIG. 2 shows the injection plunger 13 provided with the shielding device 24 in a position almost fully withdrawn from the syringe 10. When the injection plunger 13 is pushed into the syringe the shielding device 24 enters into the tubular portion 26 and is received therein.

Figure 3:
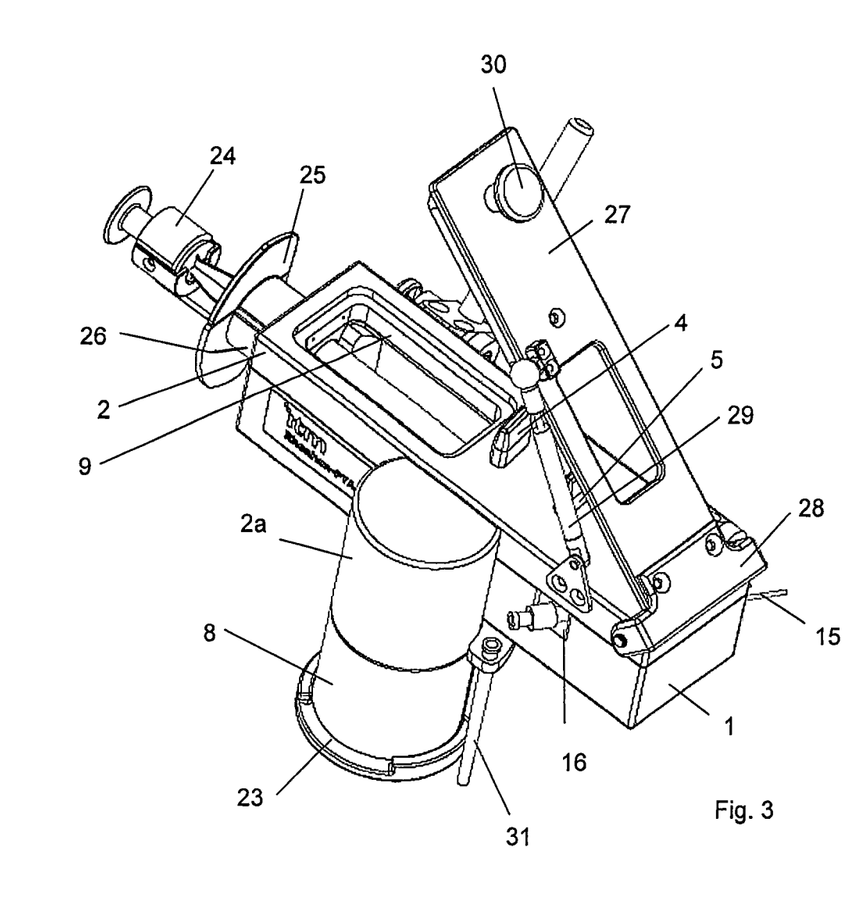
FIG. 3 shows the apparatus according to the invention as in FIG. 2, yet with an open flap.
Figure 4:
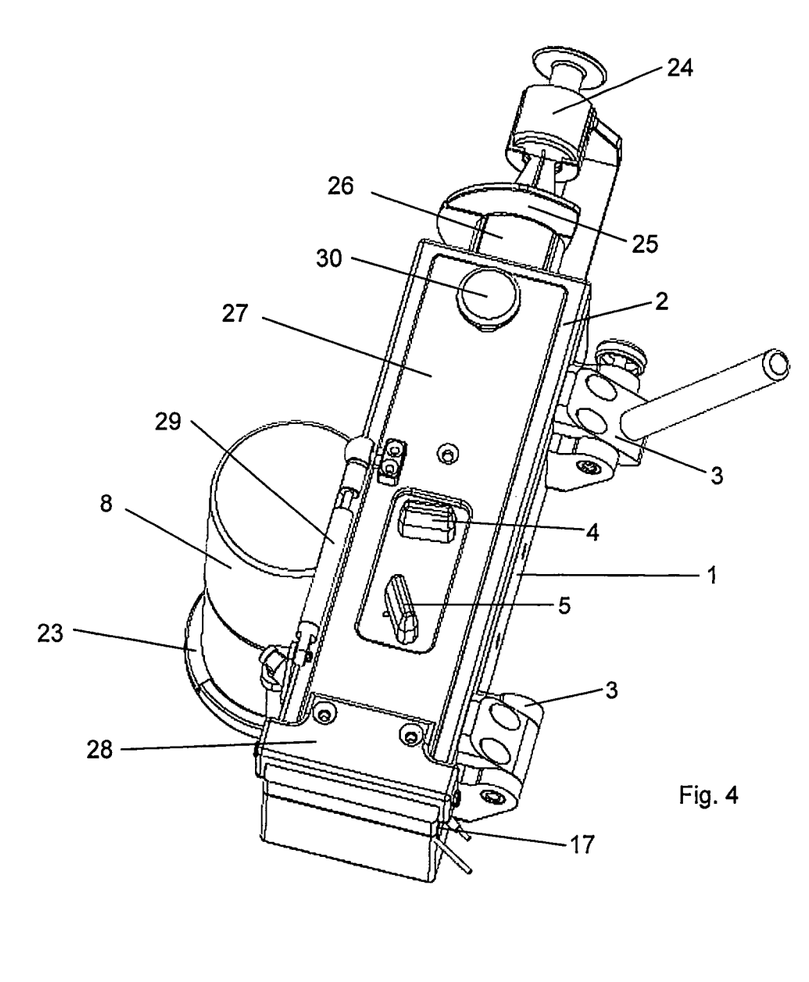
FIG. 4 shows the apparatus according to the invention in accordance with the embodiment shown in FIG. 1, in closed position and a different perspective side elevation.

The lid 2 further is provided with a flap 27 for closing the window opening 9. It is mounted on the lid 2 for pivoting movement by means of hinges 28. The flap 27 includes a metal plate which can be folded down on the surface of the lid 2 opposite the housing 1. The metal plate comprises a thickened portion of the shape of the window opening 9, whereby it fills the window opening 9 when the flap 27 is lowered on the lid 2. The flap 27 moreover includes an opening 28 through which pass the rotary levers 4 and 5. A telescopic arm 29 is fixed to the flap 27 and the lid 2, as shown in FIG. 3, to limit the pivoting movement of the flap and allow it to be held in open position. A knob 30 is likewise mounted on the flap 27 to facilitate opening and closing of the flap 27. A mirror (not shown) may be provided at the inner side of the flap 27, more particularly on the thickened portion, to allow the syringe 10 in the housing 1 to be observed when the flap 27 is partly open.

The apparatus has a length of approximately 20 cm, a height of approximately 3 cm, and a width of approximately 7 cm. The wall thickness of the housing is about 0.75 cm. The dimensions may be selected to be smaller or greater.

The apparatus may be put to use in the following manner. First, a syringe 10 is introduced into the housing 1. Subsequently the end and branched piece, respectively, of a catheter 15 are positioned in the housing 1 and interconnected through the valves 19, 21 by means of tube sections 18, 20. Finally, a receptacle 8 containing a radioactive liquid destined for treatment is introduced into the take-up 23 of the apparatus and connected at the three-way valve 21 to the syringe 10 and to the catheter 15. Thereupon, the housing 1 is closed by the lid 2. This causes the fixtures 6 and 7 of the rotary levers 4 and 5 to engage the levers of the valves 19 and 21. The apparatus thus is prepared for use.

In a first step of application, the syringe 10 is filled with the liquid contained in the receptacle 8, the valves 19, 21 being set so that the catheter 15 is uncoupled. When the syringe 10 has been filled valve 21 is switched so that the receptacle 8 is uncoupled. Having switched valve 19, the contents of the syringe 10 now can be pressed into the catheter 15 by pushing the injection plunger 13 provided with the shielding device 24. Monitoring of the filling process of the syringe is possible by observing the syringe through the open window 9 and, if desired, making use of the mirror mounted on the flat 27. The entire process of filling the catheter 15 takes place under shielding by the housing 1 and the lid 2, respectively, and, if desired, while using the shielding device 24 for the injection plunger 13. Hereby the radiation escaping to persons nearby is nearly reduced.

Numerous modifications may be made to the embodiment described above without leaving the scope of the instant invention. For instance, the syringe 10 can be completely inside the housing 1 and to accomplish the drawing in and filling and emptying, respectively, of the syringe 10 with the assistance of a motor. Moreover, the receptacle 8 might be arranged and fixed, respectively, within the housing 1. Several facilities for take-up of receptacles can be provided at or in the housing.

Moreover, a support may be fastened to the housing 1, offering an opportunity to place the apparatus on a base together with the receptacle 8 joined to the apparatus. The support may be secured to the housing 1 by a holding device 31 in such manner that the housing is inclined with respect to the base so that, when filling the catheter, air bubbles in the syringe will rise towards the end of thereof and be prevented from getting into the catheter.

Likewise, the housing 1 may have a structure which allows a medical instrument or a catheter to be fully housed inside and with no need to provide openings in the housing 1 to permit passage of a catheter.

As far as the connection between the receptacle 8 and the syringe 10 and the catheter 15 is concerned other realizations can be implemented. For instance, the coupling between the receptacle and the housing could be implemented by an automatic interface. And the lid 2 could be provided without the projecting portion 2a for the receptacle 8 if, at the same time, a fully shielded receptacle 8 is used.

The features indicated in the specification above and in the claims may be important to the invention in any desired combination.

The invention claimed is:

1. An apparatus for filling a medical instrument with a radioactive substance, comprising:
  a housing, wherein the housing is configured to removably receive a body of a syringe having the body and an injection plunger projecting from the body, wherein the housing is configured to receive at least a part of a medical instrument, wherein the housing is configured to shield against radioactive radiation, wherein the housing comprises a first opening configured to receive the injection plunger projecting from the body such that the injection plunger protrudes from inside the housing to outside the housing;
  a shielding device, wherein the shielding device is configured to be connected with an end of the injection plunger projecting from the body and protruding from inside the housing to outside the housing to shield the end of the injection plunger; and
  a take up device, wherein the take up device is configured to receive a receptacle for a radioactive substance, wherein the take up device is arranged at the housing, wherein the housing further comprises:
    a lid, wherein the lid covers or closes the housing and the receptacle for a radioactive substance received by the take up device arranged at the housing; and
    wherein the first opening is formed in a wall of the housing and is open to an edge of the wall so that the first opening is configured to receive a portion of the injection plunger projecting from the body into the first opening from the edge of the wall, and wherein the first opening allows actuation of the injection plunger of the syringe the body of which is received by the housing.

2. The apparatus as claimed in claim 1, wherein the take up device is configured for the receptacle for a radioactive substance to be arranged and fastened outside of the housing, wherein the housing further comprises a second opening, wherein the second opening allows a connection to be made from the receptacle for a radioactive substance into the housing.

3. The apparatus as claimed in claim 1, wherein the housing further comprises a means for manipulating a valve disposed inside the housing, wherein the means for manipulating the valve is actuatable from outside the housing.

4. The apparatus as claimed in claim 1, wherein the housing is made of a material that shields radioactive radiation.

5. The apparatus as claimed in claim 1, wherein the housing is made of tungsten.

6. The apparatus as claimed in claim 1, wherein the housing comprises a window.

7. The apparatus as claimed in claim 6, wherein the housing comprises a flap, wherein the flap is adapted to close the window.

8. The apparatus as claimed in claim 1, wherein the housing is configured to secure the syringe and the at least a part of the medical instrument, wherein the housing is configured to receive and secure one or more valves and connecting lines.

9. The apparatus as claimed in claim 1, wherein the housing comprises a third opening, wherein the third opening allows passage of the medical instrument.

10. The apparatus as claimed in claim 1, further comprising:
  a support, wherein the support is connected to the housing in such a way that the apparatus and the body received inside the housing are inclined with respect to a base surface.

11. The apparatus as claimed in claim 1, wherein the medical instrument is a catheter.

12. The apparatus according to claim 1, wherein when the lid is open the syringe can be removed from or inserted into the housing, wherein when the lid is closed the syringe cannot be removed from or inserted into the housing.

13. The apparatus according to claim 1, wherein the housing comprises a holding surface forming an extension of the housing and at least partially surrounding the injection plunger when the body is received by the housing and the injection plunger is projecting from the body.

14. The apparatus according to claim 13, wherein the shielding device forms an extension of the injection plunger so that a finger pressing on the shielding device, instead of the end of the injection plunger, is at a greater distance from the body.

15. The apparatus according to claim 1, wherein the shielding device forms an extension of the injection plunger so that a finger pressing on the shielding device, instead of the end of the injection plunger, is at a greater distance from the body.

16. A system for filling a medical instrument with a radioactive substance, comprising:
a syringe having a body and an injection plunger projecting from the body;
a receptacle for a radioactive substance; and
an apparatus, wherein the apparatus comprises:
a housing, wherein the housing is configured to removably receive the body, wherein the housing is configured to receive at least a part of a medical instrument, wherein the housing is configured to shield against radioactive radiation, wherein the housing comprises a first opening configured to receive the injection plunger projecting from the body such that the injection plunger protrudes from inside the housing to outside the housing;
a shielding device, wherein the shielding device is configured to be connected with an end of the injection plunger projecting from the body protruding from inside the housing to outside the housing to shield the end of the injection plunger; and
a take up device, wherein the take up device is configured to receive the receptacle for a radioactive substance, wherein the take up device is arranged at the housing,
wherein the housing further comprises:
a lid, wherein the lid covers or closes the housing and the receptacle for a radioactive substance received in the take up device arranged at the housing; and
wherein the first opening is formed in a wall of the housing and is open to an edge of the wall so that the first opening is configured to receive a portion of the injection plunger projecting from the body into the first opening from the edge of the wall, and wherein the first opening allows actuation of the injection plunger of the syringe the body of which is received by the housing.

17. The system as claimed in claim 16, further comprising:
a valve disposed in the apparatus;
the medical instrument arranged at least partly in the apparatus; and
hose sections for connecting the syringe, the valve, the receptacle for a radioactive substance, and the medical instrument.

18. The system as claimed in claim 16, wherein the receptacle for a radioactive substance is removably attachable to the apparatus.

19. The system according to claim 16, wherein when the lid is open the syringe can be removed from or inserted into the housing, wherein when the lid is closed the syringe cannot be removed from or inserted into the housing.

20. The system according to claim 16, wherein the housing comprises a holding surface forming an extension of the housing and at least partially surrounding the injection plunger when the body is received by the housing and the injection plunger is projecting from the body.

21. The system according to claim 20, wherein the shielding device forms an extension of the injection plunger so that a finger pressing on the shielding device, instead of the end of the injection plunger, is at a greater distance from the body.

22. The system according to claim 16, wherein the shielding device forms an extension of the injection plunger so that a finger pressing on the shielding device, instead of the end of the injection plunger, is at a greater distance from the body.

23. A method for filling a medical instrument with a radioactive substance, using an apparatus comprising:
a housing, wherein the housing is configured to removably receive a body of a syringe having the body and an injection plunger projecting from the body, wherein the housing is configured to receive at least a part of a medical instrument, wherein the housing is configured to shield against radioactive radiation, wherein the housing comprises a first opening configured to receive the injection plunger protruding from the body such that the injection plunger protrudes from inside the housing to outside the housing;
a shielding device, wherein the shielding device is configured to be connected with an end of the injection plunger projecting from the body and protruding from inside the housing to outside the housing to shield the end of the injection plunger; and
a take up device, wherein the take up device is configured to receive a receptacle for a radioactive substance, wherein the take up device is arranged at the housing, wherein the housing further comprises:
a lid, wherein the lid covers or closes the housing and the receptacle for a radioactive substance received by the take up device arranged at the housing; and
wherein the first opening is formed in a wall of the housing and is open to an edge of the wall so that the first opening is configured to receive a portion of the injection plunger projecting from the body into the first opening from the edge of the wall, and wherein the first opening allows actuation of the injection plunger of the syringe; the body of which is received by the housing,
wherein the method further comprises:
inserting the body into the housing such that the injection plunger projecting from the body is introduced into the first opening from the edge of the wall;
connecting the shielding device with the end of the injection plunger;
drawing the radioactive substance into the syringe while using the shielding device to shield the end of the injection plunger;
filling the medical instrument with the radioactive substance from the syringe; and
removing the body from the housing.

24. The method as claimed in claim 23, further comprising:
arranging at least a part of the medical instrument in the housing.

25. The method as claimed in claim 23, further comprising:
returning the radioactive substance from the medical instrument into the syringe.

26. The method as claimed in claim 23, further comprising:
returning the radioactive substance from the medical instrument into the receptacle for a radioactive substance.

27. The method according to claim 23, wherein when the lid is open the syringe can be removed from or inserted into the housing, wherein when the lid is closed the syringe cannot be removed from or inserted into the housing.

28. The method according to claim 23, wherein the housing comprises a holding surface forming an extension of the housing and at least partially surrounding the injection plunger when the body is received by the housing and the injection plunger is projecting from the body.

29. The method according to claim 28, wherein the shielding device focus an extension of the injection plunger so that a finger pressing on the shielding device, instead of the end of the injection plunger, is at a greater distance from the body, wherein filling the medical instrument with the radioactive substance from the syringe comprises pressing on the shielding device at a location being at a greater distance from the body than the end of the injection plunger.

30. The method according to claim 23, wherein the shielding device forms an extension of the injection plunger so that a finger pressing on the shielding device, instead of the end of the injection plunger, is at a greater distance from the body, wherein filling the medical instrument with the radioactive substance from the syringe comprises pressing on the shielding device at a location being at a greater distance from the body than the end of the injection plunger.

* * * * *

UNITED STATES PATENT AND TRADEMARK OFFICE
CERTIFICATE OF CORRECTION

PATENT NO.         : 8,734,315 B2                                             Page 1 of 1
APPLICATION NO.    : 12/526429
DATED              : May 27, 2014
INVENTOR(S)        : Michael Schilp, Tuomo Kaarlo Nikula and Oliver Buck It is certified that error appears in the above-identified patent and that said Letters Patent is hereby corrected as shown below:

In the Specification

Column 4,
Line 20, "a salve disposed" should read --a valve disposed--.
Line 29, "instrument big the" should read --instrument by the--.

Column 5,
Line 17, "rotary, levers" should read --rotary levers--.

Column 6,
Lines 14-15, "that this manner" should read --that in this manner--.

Column 7,
Line 13, "on the flat" should read --on the flap--.
Line 18, "is nearly reduced." should read --is clearly reduced.--.

In the Claims

Column 10,
Line 63, Claim 29, "device focus an extension" should read --device forms an extension--.

Signed and Sealed this
Eleventh Day of November, 2014

Michelle K. Lee
*Deputy Director of the United States Patent and Trademark Office*